United States Patent [19]

Claeson et al.

[11] Patent Number: 5,574,014

[45] Date of Patent: Nov. 12, 1996

[54] INHIBITORS OF TRYPSIN-LIKE ENZYMES

[75] Inventors: Goran Claeson, London, England; Manfred H. W. Philipp, Scarsdale, N.Y.; Rainer Metternich, Inzlingen, Germany

[73] Assignee: Thrombosis Research Institute, London, United Kingdom

[21] Appl. No.: 240,606

[22] Filed: May 10, 1994

Related U.S. Application Data

[63] Continuation of Ser. No. 998,632, Dec. 30, 1992, abandoned, which is a continuation of Ser. No. 795,219, Nov. 20, 1991, abandoned, which is a continuation of Ser. No. 680,496, Apr. 4, 1991, abandoned, which is a continuation of Ser. No. 406,663, Sep. 13, 1989, abandoned, which is a continuation-in-part of Ser. No. 181,511, Apr. 28, 1988, abandoned.

[30] Foreign Application Priority Data

Feb. 2, 1989 [GB] United Kingdom .................. 8902304

[51] Int. Cl.$^6$ .............. A61K 38/00; C07K 5/00; C07K 7/00; C07K 16/00
[52] U.S. Cl. ............... 514/18; 514/19; 530/331; 530/330
[58] Field of Search ................ 514/17, 18, 19; 530/330, 331

[56] References Cited

U.S. PATENT DOCUMENTS

| | | | |
|---|---|---|---|
| 4,428,874 | 1/1984 | Svendsen | 260/112 |
| 4,450,105 | 5/1984 | Nagasawa et al. | 260/112 |
| 4,638,047 | 1/1987 | Szelke et al. | 530/332 |

FOREIGN PATENT DOCUMENTS

| | | |
|---|---|---|
| 0471651A2 | 2/1992 | European Pat. Off. . |
| WO94/20526 | 9/1994 | WIPO . |

OTHER PUBLICATIONS

Bajusz, S., et al. (1978) *Int. J. Peptide and Protein Res.*, 12:217–221. Inhibition of Thrombin and Trypsin by Tripeptide Aldehydes.

Chang, J.–Y, (1985) *Eur. J. Biochem.* 151:217–224. Thrombin specificity.

*Primary Examiner*—Avis M. Davenport
*Attorney, Agent, or Firm*—Townsend and Townsend and Crew LLP

[57] ABSTRACT

Pharmaceutical compositions comprising compounds of the formula:

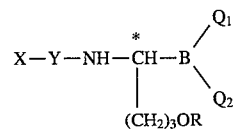

in which X=H or is an N-protecting group; Y is Phe-Pro; $Q_1$ and $Q_2$ taken together represent the residue of a diol; R is $C_{1-4}$ alkyl; and the asymmetric carbon atom marked * may have the D- or L- configuration, are useful in therapeutic methods of inhibiting thrombin.

14 Claims, 4 Drawing Sheets

INHIBITORS OF TRYPSIN-LIKE ENZYMES

This is a continuation of application Ser. No. 998,632 filed Dec. 30, 1992 now abandoned, which is a continuation of application Ser. No. 795,219 filed Nov. 20, 1991 now abandoned, which is a continuation of application Ser. No. 680,496 filed Apr. 4, 1991 now abandoned, which is a continuation of application Ser. No. 406,663 filed Sep. 13, 1989 now abandoned, which is a continuation-in-part of application Ser. No. 181,511 filed Apr. 28, 1988 and now abandoned.

This invention relates to thrombin inhibitors. Thrombin, the last enzyme in the coagulation system, cleaves soluble fibrinogen to fibrin, which is then crosslinked and forms an insoluble gel forming the matrix for a thrombus. When a vessel is damaged, the above process is necessary to stop bleeding. Under normal circumstances there is no measurable amount of thrombin present in plasma. Increase of the thrombin concentration can result in formation of clots, which can lead to thromboembolic disease, one of the most common serious medical problems of our time.

Thrombin contributes to haemostatic control by means of several biological reactions. In addition to its primary function, the conversion of fibrinogen to fibrin, thrombin activates Factor XIII, which is responsible for the crosslinking of fibrin. Thrombin also acts by means of a positive feed back mechanism involving the activation of Factors V and VIII, which both are necessary for its own formation from prothrombin. Thrombin has another essential role: its binding to platelets inititates platelet release and aggregation which is responsible for primary haemostasis.

The role and regulation of thrombin in thrombogenesis is summarized schematically in FIG. 1. The reactions of thrombin are further controlled by natural inhibitors in plasma. The most important of these are antithrombin III and heparin. These two compounds have been isolated and are therapeutically and prophylactically used in conditions where there is an imbalance in the haemostatic mechanism with risk for prothrombin activation.

Synthetic thrombin inhibitors, having oral activity, would be useful as alternatives to the parenteral administration of these natural inhibitors. Much research in this area has resulted in the synthesis of good inhibitors of thrombin in vitro, but as yet there is no really good candidate for oral therapeutic use. By imitating amino acid sequences of fibrinogen, the important natural substrate of thrombin, several good short peptide substrates for thrombin have been produced. These peptide substrates have also been transformed into inhibitors of the enzyme. Thus, the chromogenic substrates D-Phe-Pro-Arg-pNA and D-Phe-Pip-Arg-PNA mimic the sequence preceding the bond split by thrombin. The corresponding reversible and irreversible inhibitors, D-Phe-Pro-Arginal and D-Phe-Pro-Arg-CH$_2$Cl show inhibition in vitro in the $10^{-8}$M range.

Chloromethylketones are generally too nonspecifically reactive to be ideal for therapeutic use, and the peptide aldehyde exemplified above has quite a low LD$_{50}$ value.

Factor Xa is the coagulation enzyme responsible for the generation of thrombin by limited proteolysis of its zymogen, prothrombin. On a weight for weight basis factor Xa is at least 10 times more thrombogenic in vivo than thrombin. This arises from the fact that factor Xa is one step above thrombin in the amplifying cascade system, so that one molecule of factor Xa can generate many molecules of thrombin from its precursor. Its potency may also arise from the rather slow removal of factor Xa by the body. Thrombin, unlike factor Xa, is rapidly cleared from circulating blood onto high affinity sites on the vessel wall. The central position of factor Xa at the junction of the intrinsic and the extrinsic pathways should make it a suitable target for modulating the haemostatic mechanism.

Kallikrein is formed from prekallikrein by the action of factor XII, when located on a negatively charged surface. Kallikrein in turn can cleave factor XII to factor XIIa, thereby forming a reciprocal activation system. Factor XIIa is the first enzyme of the intrinsic part of the coagulation system. The significance of the contact system is probably as a surface mediated defense mechanism, and a large scale activation of the system is normally seen during shock or disseminated intravascular coagulation (DIC). The role of kallikrein at this stage is to cleave high molecular weight kininogen with the release of the vasodilator, bradykinin. Bradykinin also causes increased vascular permeability, pain and migration of the neutrophil leucocytes. Inhibitors of kinin formation have been shown to be beneficial in certain types of inflammation, including arthritis and pancreatitits, and may be useful also in the treatment of asthma. The only substance that has attained clinical significance as a kallikrein inhibitor, is aprotinin (Trasylol). Aprotinin is a polypeptide of molecular weight 6.500, and forms a stable complex with proteases, having a binding constant of $10^{-10}$–$10^{-13}$M.

Fibrinolysis is the process which causes an enzymatic dissolution of fibrinogen and fibrin clots. Plasma contains a protein, plasminogen, which under the influence of various activators is converted to plasmin, a proteolytic enzyme, the activity of which resembles that of trypsin. Plasmin breaks down fibrinogen and fibrin to fibrin/fibrinogen degradation products.

Under normal conditions, the fibrinolysis system is in balance with the coagulation system. Small thrombi formed in the blood stream can be dissolved enzymatically and the circulation through the vessels can be restored by the activation of the fibrinolytic system in the body. If the fibrinolytic activity is too high, it may cause or prolong bleeding. The activity can be inhibited by natural inhibitors in the blood.

Boronic acids have been studied as inhibitors of various serine esterases and proteases. The first boronic acid-containing amino acid analog to be used as a protease inhibitor was the boronic acid analog of N-acetyl L-phenylalanine, which was used as an inhibitor of chymotrypsin and subtilisin. Peptide boronic acids have been used as inhibitors of chymotrypsin, subtilisin, and elastases.

The interaction of boronic acids with proteases in biological systems is known and various simple boronic acids have been shown to be sufficiently nontoxic for use in humans. Peptide boronic acid inhibitors of elastase have recently been used in animal trials in relation to emphysema. Unlike the peptide chloromethylketones, there was no toxicity reported at biologically effective dosage levels. The parent application, Ser. No. 181,511, described the preparation of the boroarginine compound Z-D-Phe-Pro-boroArg. This compound name corresponds to the structure of formula I

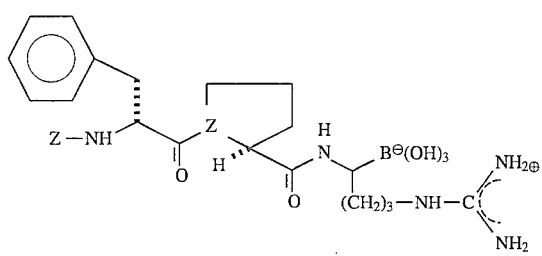

in which Z is

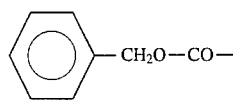

or, in protected form, of formula II

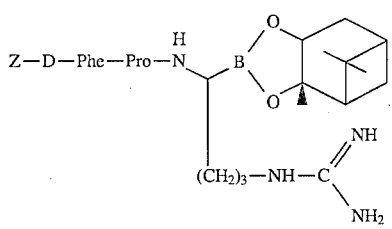

where Z is as stated above

D-Phe is

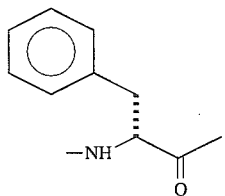

and Pro is

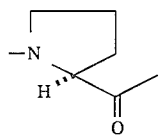

The compound was described as being produced by the synthetic route:

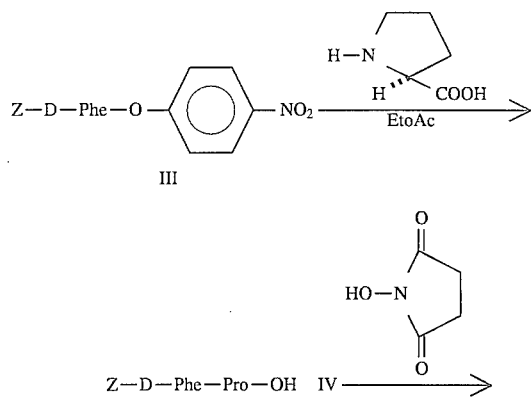

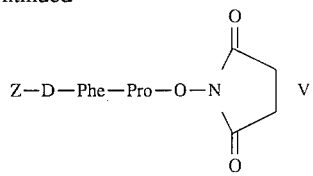

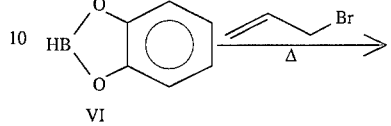

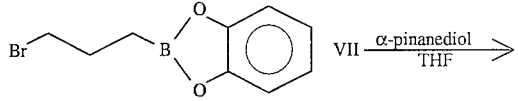

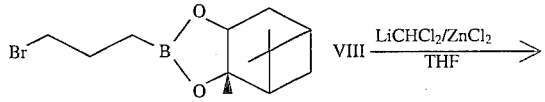

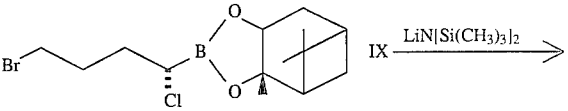

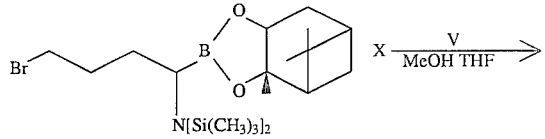

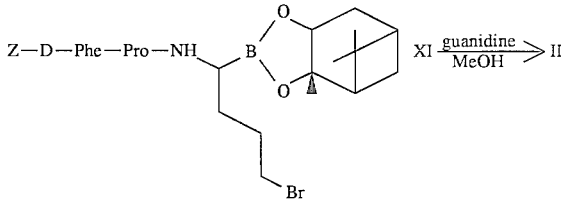

However, it has now been found that the product of this synthesis is not the above structure II but the methoxy compound of formula XII

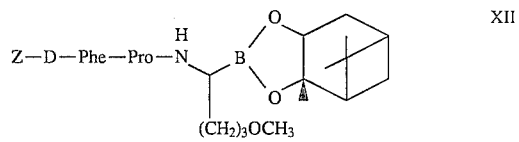

and although the product does not have the structure previously assigned to it, it is nevertheless a strong thrombin inhibitor.

The proton NMR spectrum of the product, which was appended as FIG. 3 of the parent application, and is reproduced as FIG. 2 of the present application, is indeed consistent with the structure of formula XII, as it shows a strong singlet peak at 3.25 ppm attributable to the methoxy group.

SUMMARY OF THE INVENTION

Figure 1:
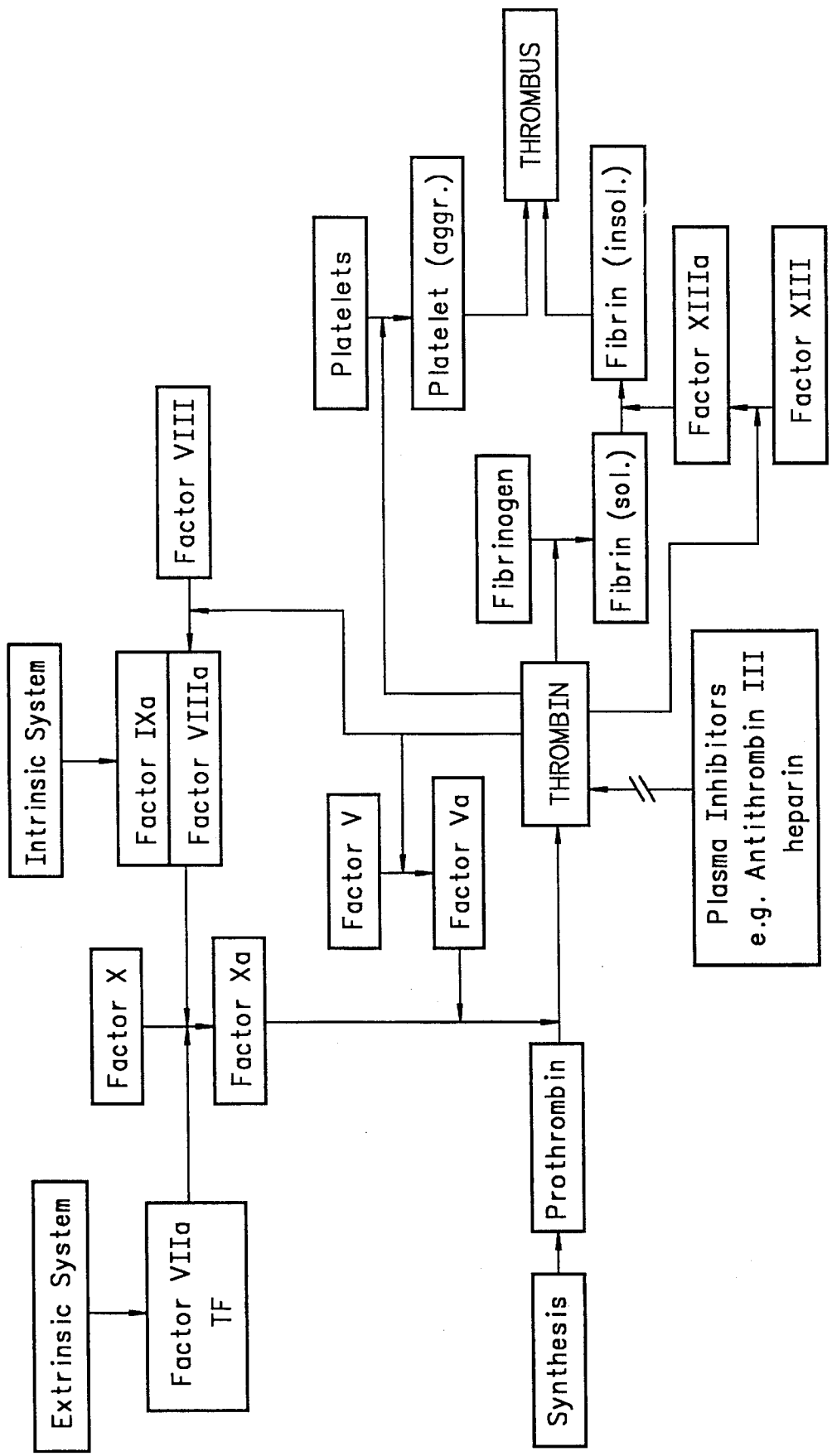
FIG. 1 depicts the role and regulation of thrombin in thrombogenesis.
Figure 2:
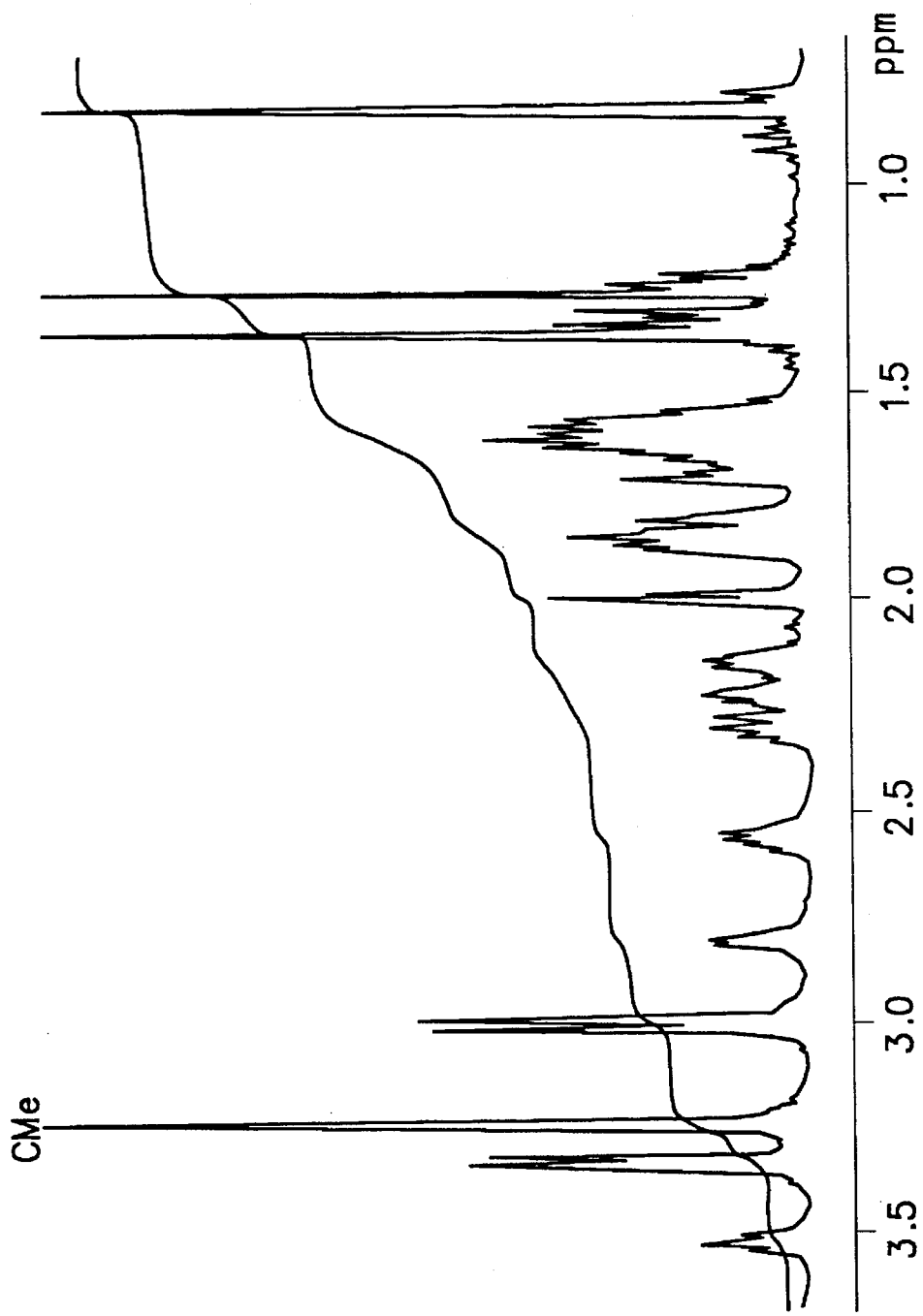
FIG. 2 depicts a proton NMR from 0 ppm to 3.5 ppm of the compound of formula XII, herein.

Accordingly, the present invention provides compounds of formula XIII

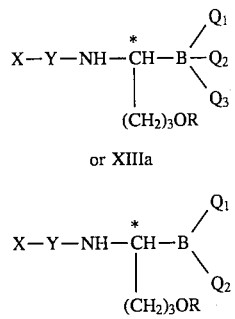

in which X=H or is an N-protecting group;
Y is a sequence of n amino acids selected such that the n+1 amino acid peptide Y-Lys or Y-Agr has an affinity for the active site of a trypsin-like protease, where n is an integer from 1 to 10 preferably 1 to 4;
$Q_1$, $Q_2$ and $Q_3$, which may be the same or different, are selected from the group consisting of —OH, —$COR_1$, —$CONR_1R_2$, —$NR_1R_2$, and —$OR_3$, or $Q_1$ and $Q_2$ taken together represent the residue of a diol; where $R_1$, $R_2$ and $R_3$, which may be the same or different, are $C_{1-10}$ alkyl, $C_{6-10}$ aryl aralkyl, or phenyl substituted by up to three groups selected from $C_{1-4}$ alkyl, halo and $C_{1-4}$ alkoxy;
R is $C_{1-4}$ alkyl, preferably methyl;
and the asymmetric carbon atom marked * may have the D- or L-configuration, or represent any mixture of these.

Preferably the N-protecting group X is of formula $R_6CO$—, $R_7OCO$— or $R_8SO_2$— in which $R_6$ is $C_{1-6}$ alkyl; $R_7$ is $C_{1-6}$ alkyl; phenyl or naphthyl; and $R_8$ is phenyl, naphthyl or $C_{1-4}$ alkylphenyl. The most preferred protecting group is benzyloxycarbonyl of formula $C_6H_5CH_2OCO$—, designated Z in formulae I–V and XI–XIII above.

Preferred compounds are those of formula XIIIa in which $Q_1$ and $Q_2$ are —$OR_4$ and —$OR_5$ wherein $R_4$ and $R_5$ represent the residue of a dihydroxy compound. Useful examples are, 2,3-butanediol; catechol; 2,3-dimethylbutan-diol-2,3; cyclohexanediol; ethylene glycol; 1,2-hexanediol; 2,3-hexanediol; diethanolamine or aliphatic or aromatic compounds having hydroxy groups that are substituted on adjacent carbon atoms or on carbon atoms substituted by another carbon.

Particularly preferred are those compounds in which $Q_1$ and $Q_2$ taken together represent the group OPin of formula

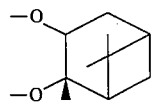

The peptide boronic acid pinanediol ester may be converted to the free acid form by the method described by H. C. Brown, *J. Organomet. Chem.* 358, 15, (1988), in which the pinanediol boronate is first reacted with one equivalent of methyllithium and subsequently with HCl and methanol to give a borinate ester containing the group

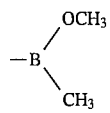

Treatment of this with $I_2$/NaOMe in THF gives the dimethyl boronate ester, which hydrolyses readily in water to the free acid.

The amino acids constituting Y are α-amino acids which may be selected from the L-amino acids naturally occurring in proteins, their corresponding enantiomeric D-amino acids or chemically modified alpha-amino acids such as glutamic acid gamma-piperidide

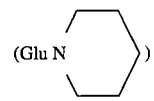

or pipecolic acid (Pip).

DETAILED DESCRIPTION OF THE INVENTION

The trypsin-like enzymes are those proteolytic enzymes that are capable of hydrolyzing a peptide bond at the carboxylate group of Lys or Arg. This capability may be evaluated by testing the susceptibility of benzoyl lysine ethyl ester or benzoylarginine ethyl ester (0.1 mM) to hydrolysis by enzyme in I=0.2M phosphate buffer pH 7.0 at 37° C. while observing optical absorbance at 255 nm to detect an increase in optical density which is greater than the increase found in the absence of enzyme.

Examples of such enzymes are trypsin, thrombin, factor Xa, factor IXa, factor VIIa, factor XIIa, plasmin, acrosin, complement proteases, kallikrein, urokinase (UK) and tissue plasminogen activator (TPA). Examples of peptide sequences for some of these enzymes are set forth in Table 1:

TABLE 1

| Enyzme | Peptide (Y) |
| --- | --- |
| Thrombin | —D—Phe—Pro— |
| Factor Xa | Ile—Glu[N⟩]—Gly— |
| Kallikrein | —Phe— or —D—Pro—Phe— |
| UK or TPA | —Gly—Gly— |

A peptide is considered to have an affinity for the active site of trypsin-like proteases if the particular peptide has a value of $10^{-3}M$ or lower for the dissociation constant as measured in Procedure G.

The compounds of formula XIIIa may be prepared by the reaction of a compound of formula XIV

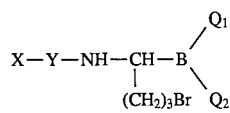

in which X, Y, $Q_1$ and $Q_2$ are as defined above, with an alcohol of formula R—OH at temperatures of from 0°–50° C. preferably at room temperature, and in the presence of guanidine. The guanidine may be generated from a guanidine salt by adding alkali, for example NaOMe.

The compounds of formula XIV may be obtained by the reaction of a compound of formula X—Y—W in which W represents an active ester group, with a compound of formula XV

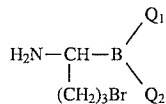

XV in which $Q_1$ and $Q_2$ are as defined above. The compound XV is not isolated, but is formed in situ by the reaction of $LiN[Si(CH_3)_3]_2$ with a compound of formula XVI

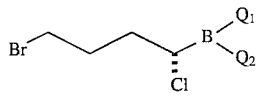

XVI and subsequent treatment with 2 moles of methanol.

The reaction is preferably carried out in a dry aprotic polar solvent, for example THF, at a temperature between −78° C. and room temperature.

In the compound of formula X—Y—W, the active ester group W is preferably an N-hydroxysuccinimide or pentafluorophenol residue. The compound X—Y—W may be prepared by methods conventional in peptide chemistry.

The compounds of formula XIII or XIIIa are useful as inhibitors of trypsin-like proteases and may be used in vitro for diagnostic and mechanistic studies of these enzymes. Furthermore, because of their inhibitory action they are indicated for use in the prevention or treatment of diseases caused by an excess of an enzyme in a regulatory system, for example control of the coagulation or fibrinolysis system.

Those compounds of the invention which are thrombin or factor Xa inhibitors have anti-thrombogenic properties and may be employed for indications when an anti-thrombogenic agent is indicated. Generally, these compounds may be administered orally or parenterally to a host to obtain an anti-thrombogenic effect. In the case of larger mammals such as humans, the compounds may be administered alone or in combination with pharmaceutical carrier or diluent at a dose of from 0.02 to 15 mg/Kg of body weight and preferably 1–10 mg/Kg to obtain the anti-thrombogenic effect, and may be given as single dose or in divided doses or as a sustained release formulation. When an extracorporeal blood loop is to be established for a patient, 0.1–1 mg/Kg may be administered intravenously. For use with whole blood from 1–10 mg per liter may be provided to prevent coagulation. Pharmaceutical diluents are well known and include sugars, starches and water which may be used to make tablets, capsules, injectable solutions and the like. The compounds of the invention may be added to blood for the purpose of preventing coagulation of the blood in blood collecting or distribution containers, tubing or implantable apparatus which comes in contact with blood.

The advantages of the compounds of the invention include oral activity, rapid onset of activity and low toxicity. In addition, these compounds may have special utility in the treatment of individuals who are hypersensitive to compounds such as heparin.

In the following examples, the symbols have the following meanings:

| | |
|---|---|
| Z = | benzyloxycarbonyl |
| Ac = | acetyl |
| MeOH = | methyl alcohol |
| EtOAc = | ethyl acetate |
| DCC = | dicyclohexylcarbodiimide |
| HONSu = | N-hydroxy-succinimide |
| PfpOH = | pinanediol |
| NMR = | nuclear magnetic resonance |
| THF = | tetrahydrofuran |
| n-Bu = | n-butyl |
| NP = | p-nitrophenyl |
| Boc = | t-butyloxycarbonyl |
| PfpOH = | pentafluorophenyl |
| TLC = | thin layer chromatography |
| Bzl = | benzyl |
| Baa = | —NH—CH—($CH_2CH_2CH_2Br$)B— |
| BOMe = | —NH—CH—($CH_2CH_2CH_2OCH_3$)B— |

Procedures A–F show the preparation of intermediates for the practice of the invention, and Procedure G describes the measurement of the dissociation constant.

PROCEDURE A

Z-D-Phe-Pro-ONSu

Z-D-Phe-ONp (5.0 g, 11.9 mmol) is dissolved in EtOAc and excess proline is added. The reaction is followed by TLC and when all ester is reacted, more EtOAc is added and the solution is extracted several times with 2% $KHSO_4$. The organic phase is dried over $Na_2SO_4$, the volume reduced and the dipeptide precipitated by the addition of petroleum ether. The precipitate is dried and purity checked by TLC.

The dipeptide (Z-D-Phe-Pro-OH) is dissolved in EtOAc, cooled to 0° C. and 20% excess of HONSu and 1-(3-dimethyl-aminopropyl)-3-ethyl carbodiimide are added. After 4 hours, the solution is allowed to reach room temperature and left to react overnight. The solution is washed several times with base (0.1M $Na_2CO_3$), acid (2% $KHSO_4$) and water and the organic phase is dried over $Na_2SO_4$, the solvent removed, the active ester redissolved in ether and precipitated by the addition of petroleum ether. The purity is checked by TLC.

PROCEDURE B

Z-Gly-Gly-O-Pfp

Z-Gly-Gly OH (2.1 g, 8.0 mmol) and PfPOH (1.5 g (8.0 mmol)) are dissolved in 45 ml of EtOAc: DMF (1:1) and the solution is cooled to 0° C. DCC (1.6 g, 8.0 mmol) is added under vigorous stirring and the reaction is left for 1 hour at 0° C. and after a further 3 hours at room temperature TLC indicates that the reaction is complete. Dicyclohexylurea (DCU) is filtered and the solution evaporated under reduced pressure. The remaining white solid is redissolved in 20 ml of ethyl acetate, washed quickly with 1M sodium bicarbonate and water and dried over magnesium sulphate. The volume of the solution is somewhat reduced by about 50–75% and again filtered from precipitated DCU. The remaining solution is evaporated to dryness. Yield 3.2 g (92%). An analytical sample is recrystallised from ethyl acetate: n-hexane (5:1).

PROCEDURE C

Ac-Leu-Leu-OPfp

Leu-Leu (1.0 g, 3.8 mmol) and potassium carbonate (7.0 g, 5 mmol) are dissolved in 100 ml of water. The solution is cooled with ice and 5.0 ml acetic anhydride in 50 ml of ether is added dropwise under vigorous stirring. Stirring is continued for one hour, then the ice-bath is removed and the stirring continued for further 2 hours. The water phase is separated, acidified with hydrochloric acid. The precipitate is stirred for one hour, filtered, washed with water and dried yielding 0.8 gram (74%) of Ac-Leu-Leu.

The acetylated dipeptide is transformed to the active ester according to the method described in Procedure B, Yield 89%. TLC shows the presence of a small amount of DCU.

PROCEDURE D

Z-Phe-O-Pfp

The active ester is obtained from Z-Phe-OH according to the method described in Procedure B, Yield 91%. TLC shows the presence of a very small amount of DCU.

PROCEDURE E

Boc-Ile-Glu (γ-piperidide)-Gly-OPfp

Boc-Ile-Glu-(γ-piperidide)-Gly-OH is prepared according to an unpublished method by S. Arielly in the following way:

Boc-(γ-OBzl)Glu (1.05 mmol) is dissolved in 25 ml of DMF, cooled to $-5°$ and $Et_3N$ (1.05 mmol) added under stirring. Stirring is continued and Gly-OEt (1.0 mmol); hydroxybenzotriazole (1.05 mmol) and DCC (1.05 mmol) are added. The solution is left to react overnight. After filtration, the solvent is evaporated under reduced pressure, the residue dissolved in 20 ml EtOAc, and washed with 2×10 ml each of 0.1M $NaHCO_3$, 4% $KHSO_4$ and water. The organic phase is dried over $Na_2SO_4$ and evaporated.

The above crude product of Boc-(γ-OBzl)Glu-Gly-OEt is dissolved in 10 ml of 30% TFA in $CH_2Cl_2$ and the mixture stirred for 20 min at room temperature. After evaporation, the residue is distributed between 75 ml of EtOAc and 20 ml of 20% $K_2CO_3$ solution. The organic phase is washed with the same amount of $K_2CO_3$ solution and dried over $Na_2SO_4$. The solvent is evaporated and the product used directly in the next coupling step.

Boc-Ile-OSu (1 mmol) is dissolved in 20 ml of dioxane:water (1:1) and the above deprotected peptide ester is dissolved in 10 ml of dioxane. The two solutions are combined in a beaker and stirred overnight. The solvent is then evaporated at reduced pressure, the residue dissolved in 50 ml of EtOAc and washed with 0.1M $NaHCO_3$, 4% $KHSO_4$ and water. The solution is dried over $Na_2SO_4$, the EtOAc removed at reduced pressure and the remaining protected peptide ester dissolved in HOAc and hydrogenated, with 10% Pd/C as catalyst, to remove the benzyl group.

The solution is filtered, evaporated and redissolved in 20 ml of EtOAc. DCC (1 mmol) and HOSu (1 mmol) are added and the solution stirred for two hours. Piperidine (1.5 mmol) is then added and the stirring is continued overnight. The solution is filtered and washed successively with base, acid and water as described above. The organic phase is evaporated, the ester hydrolyzed for 1 hour in 20 ml of MeOH: $H_2O$ (1:1) containing 1.2 mmol of KOH. The volume of the solution is reduced, acidified with HCl, and the crude product is taken up in EtOAc, evaporated and dissolved in a small amount of EtOH (95%). This solution is applied to a column (5×100 cm) of Sephadex LH20 and chromatographed with EtOH (95%) as eluent. Fractions with pure product are pooled and the solvent removed at reduced pressure. Yield 35%. Amino acid analysis: Ile 1.1; Glu 0.98; Gly 1.0.

The above protected peptide acid, Boc-Ile-Glu-(γ-piperidide)-Gly-OH is transformed to the active ester according to the method of Procedure B. The obtained product contains two main components and some DCU. it is purified by flash chromatography on silica gel with chloroform:ethyl acetate (2:1) as solvent. Fractions with the desired product are pooled and pure except for a small contamination of the other main product mentioned above. This is isolated from the later fractions and identified as the diketopiperazine derivative of the starting material.

PROCEDURE F

N-Z-L-Phe-ONSu

To a solution of HONSu (3.3 mmol, 0.385 g) in dioxane (50 ml) is added Z-L-Phe (3.3 mmol, 1 g). To the stirred solution is added DCC (3.3 mmol, 0.69 g). The suspension is cooled in an ice bath for 1 hr, then stored at 4° C. overnight. The solid is filtered, washed with dioxane (300 ml), and the filtrate concentrated to give 2.08 g of solid. The solid is recrystallised from $CHCl_3$ / hexane to give a white powder of m.p. 139°–140° C. (Lit. 140°–141° C.), 0.91 g, 68.4% yield. A second crop of crystals is obtained from the mother liquor.

PROCEDURE G

The dissociation constant is determined by the inhibition of the enzyme catalysed hydrolysis of a peptide-Arg-7-AMC. This hydrolysis yields 7-aminocoumarin, which is highly fluorescent. The rates of the inhibited and uninhibited reactions are determined by observing the time-dependent increase in this fluorescence. For example 2.86 μmoles of the enzyme substrate Boc-Val-Pro-Arg-7-AMC are dissolved in 10 ml of dimethylformamide. This solution is diluted 5-fold further in I=0.1M phosphate buffer; bovine serum albumin (BSA) is made up as a 1.5 mg solution in 5 ml of water. 120 NIH units of bovine thrombin or a similar amount of another enzyme are dissolved in 1 ml of pH 6.5 0.05M citrate 0.15M NaCl buffer. The enzyme solution is further diluted 100-fold in water. 0.0017 g of the peptide is dissolved in 1 ml of methanol. This solution is diluted 1000 times further in methanol. The buffer used (pH 7.0, I=0.1M phosphate,) is made according the method outlined in "The Biochemists' Handbook" (C. Long, ed., Van Nostrand, New York, 1961, p. 32).

A fluorescence spectrophotometer is set to 350 nm excitation, 440 nm emission. These are the optimal wavelength settings for the 7-aminocoumarin product. The sample chamber of the fluorescence spectrophotometer is maintained at 25° C.

The initial rate assays are performed by pipetting into a cuvette 3 ml of buffer, 80 μl of the inhibitor solution, 100 μl of BSA solution, 50; 100; 150; 200; 250 and 300 μl of the substrate solution, and finally 200 μl of the enzyme solution. The reaction is initiated by mixing the contents of the cuvette, placing it in the fluorescence spectrophotometer, and recording the time-dependent increase in fluorescence. After runs are done using different amounts of substrate solution, the results are plotted. Six determinations are done in the absence of inhibitor by adding 80 μl methanol instead of the 80 μl of inhibitor solution.

The increase in fluorescence is plotted according to the method of Lineweaver and Burke. This is done by plotting on the Y axis 1/(arbitrary fluorescence units per second) against the reciprocal molar substrate concentration, both in the absence and presence of sufficient peptide. (Sufficient peptide is a peptide concentration to make a clearly noticeable decrease in overall reaction rates at low substrate concentrations.)

In the event that the two plots (in the presence and absence of peptide) both show substantially linear relationships and produce identical intercepts on the Y axis, then the inhibitory dissociation constant $K_i$ can be derived from the slopes of the two lines using the relationship $$K_i = \frac{[I]}{\frac{(\text{slope 1})}{(\text{slope 2})} - 1}$$

where [I] is the molar peptide concentration in the cuvette, slope 1 is the Lineweaver-Burke plot slope seen in the presence of peptide and slope 2 is the Lineweaver-Burke plot slope seen in the absence of peptide.

EXAMPLE 1

A) Z-D-Phe-Pro-Baa-OPin

This example shows the coupling of the dipeptide active esters with the boron-containing precursor. All of the work is carried out under a nitrogen atmosphere. The active ester of Procedure A 1.6 g (3.1 mmol) is dissolved in 15 ml of THF and the solution cooled to −78° C. In a vessel 1.2 grams (2.6 mmol) of the compound of formula XVII

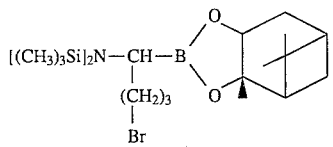

XVII are dissolved in 10 ml of THF, and then one equivalent of MeOH in THF is added. The temperature of the reaction solution is allowed to rise to 0° C. and after 4 hours the cooling bath is removed. After two days, TLC indicates that the reaction is complete, the solvent is removed and the remaining oil dissolved in CHCl$_3$:EtOAc (2:1). This solution is purified by flash chromatography on Silica gel (Merck 40–63μm) with CHCl$_3$:EtOAc (2:1) as eluent. UV-positive fractions are collected in ampules under nitrogen gas. The peptide boronic acid fractions (as judged by NMR) were pooled, the Solvent removed and the obtained oil (300 mg which is equivalent to 16%) is used for the next reaction step. The mass spectrum shows the expected molecular weight and fragmentation pattern.

B) Z-Phe-Baa-OPin 0.46 g (1 mmol) of the active ester Z-Phe-O-Pfp of Procedure D is dissolved in 4 ml of dried tetrahydrofuran and cooled to −78° C. with dry ice and acetone. The precursor XV, 0.46 g (1 mmol) dissolved in 4 ml of tetrahydrofuran (THF) is added dropwise under stirring. Finally, one equivalent of methanol dissolved in THF is added to the reaction mixture. After about 20 minutes, the temperature is raised to 0° C. and kept for 30 minutes and then again raised to room temperature. After five hours, TLC indicates that the reaction is finished. The solvent is evaporated at reduced pressure and the remaining oil is dissolved in ethyl acetate, extracted with 4% KHSO$_4$, 0.1M NaHCO$_3$ and water. The solution is dried over MgSO$_4$ and the ethyl acetate is removed at reduced pressure. The remaining oil is taken up in chloroform: ethyl acetate (2:1) and purified by flash chromatography on Silica gel (Merck 40–63μm) with the same solvent mixture as eluent. The peptide boronic acid fractions are pooled and used for the next reaction step.

Boc-Ile-Glu(γ-piperidide)-Gly-Baa-OPin, Z-Gly-Gly-Baa-OPin and Ac-Leu-Leu-Baa-Pin may also be prepared according to the above procedure.

C) Z-D-Phe-Pro-BOMe-OPin

Guanidine hydrochloride is added to an equivalent amount of MeONa in MeOH. The solution with free guanidine base is added dropwise to the above prepared Z-D-Phe-Pro-Baa-OPin (220mg, 0.30 mmole). The pH of the solution is followed and not allowed to be too high during the additions of guanidine. After three days at room temperature, the reaction mixture is neutralized with 0.1M HBr and the solvent is removed at reduced pressure. The remaining oil is dissolved in ethanol and chromatographed on Sephadex LH20 with ethanol as the mobile phase. UV positive fractions are collected under nitrogen atmosphere and the solvent is removed at reduced pressure, giving 50 mg (20%) of oily product. Amino acid analysis: Phe 0.98; Pro 1.04.

Z-Phe-BOMe-OPin, Z-Gly-Gly-BOMe-OPin, Boc-Ile-Glu(γ-piperidide)-Gly-BOMe-OPin and Ac-Leu-Leu-BOMe-OPin are synthesized according to the method described above.

Thin layer chromatography (TLC) was carried out on the following compounds using precoated silica plates (Merck, F254) in the following systems: A, chloroform-ethyl acetate (2:1); B, chloroform-methanol-acetic acid (20:4:1) and C, n-butanol-acetic acid-ethyl acetate-water (1:1:1:1). The spots were visualized by ninhydrin and chlorine-dicarboxidine spray reagents (C. M. Swahn and J. Gyllander, J. Chromatog. (1979) 170, 292:

| | RF values | | |
|---|---|---|---|
| | A | B | C |
| Ac—Leu—Leu—BOMe—OPin | 0.34 | 0.43 | — |
| Ac—Leu—Leu—Baa—OPin | 0.77 | 0.83 | — |
| Ac—Leu—Leu—OPfp | 0.30 | 0.64 | — |
| Ac—Leu—Leu—OH | 0.1 | 0.1 | 0.57 |
| Z—Phe—BOMe—OPin | 0.29 | 0.73 | — |
| Z—Phe—Baa—OPin | 0.50 | 0.80 | — |
| Z—Phe—OPfp | 0.80 | — | — |
| Boc—Ile—Glu(γ-pip)—Gly—BOMe—OPin | 0.43 | 0.60 | — |
| Boc—Ile—Glu(γ-pip)—Gly—Baa—OPin | 0.55 | 0.65 | — |
| Boc—Ile—Glu(γ-pip)—Gly—OPfp | 0.50 | — | — |
| Z—Gly—Gly—BOMe—OPin | 0.20 | 0.34 | — |
| Z—Gly—Gly—Baa—OPin | 0.33 | 0.55 | — |
| Z—Gly—Gly—OPfp | 0.35 | — | — |
| Z—D—Phe—Pro—OH | — | — | — |
| Z—D—Phe—Pro—ONSu | — | — | — |
| Z—D—Phe—Pro—Baa—OPin | 0.32 | — | — |
| Z—D—Phe—Pro—BOMe—OPin | — | — | — |
| DCU | 0.50 | — | — |

EXAMPLE 2

Improved procedure

A) Z-D-Phe-Pro-ONSu (V)

Z-D-Phe-ONp(4,2 g, 10,0 mmol) is dissolved in THF and a solution of equimolar amounts of proline and triethylamine in water is added. After 20 hr at room temperature, the THF is removed in vacuo and the aqueous residue is diluted with water and than extracted several times with EtOAc. The pH of the aqueous layer is adjusted to 3 by adding 10% citric acid. The resulting oily product is extracted several times with EtOAc. The combined organic layers are washed with water, dried over $Na_2SO_4$ and concentrated in vacuo.

The colourless oil is recrystallized from ether to give the dipeptide Z-D-Phe-Pro-OH (IV) as a white crystalline compound mp. 123°–125° C. $[\alpha]_D^{20} = -122.2°$ (C=1 in $CH_2Cl_2$).

The dipeptide (2.0 g, 5.0 mmol) is dissolved in EtOAc. After cooling to 0° C., HONSu (0.66 g, 6 mmol) and DCC (1.0 g, 5 mmol) are added. The mixture is stirred for 3.5 hr at 0° C. and then for an additional 3.5 hr at room temperature. The mixture is recooled to 0° C., the dicyclohexylurea is filtered off and washed several times with EtOAc. The filtrate is washed with aqueous 0.1M $Na_2CO_3$ and then with aqueous 2% $KHSO_4$. After drying over $Na_2SO_4$ and concentration in vacuo a colourless oil is obtained.

Recrystallization from EtOAc/ether yields the desired HO-N-Su-ester V as a white crystalline compound. m.p. 76°–78° C. $[\alpha]_D^{20} = -56.3°$ (c=1 in $CH_2Cl_2$).

B) (+) Pinanediol-3-bromopropane-1-boronate (VIII)

To catecholborane (23.8 g, 0.198 mol) under an argon atmosphere is added allylbromide (16,8 ml, 0.198 mol). The dark coloured reaction mixture is stirred at 100° C. for 4 hr. The crude material so obtained is directly distilled to give the desired catechol 3-bromopropane-1-boronate (VII). The boronic ester VII (2.41 g, 10.0 mmol) is transesterified into the optically active boronate VIII by treatment of a 0.5M solution of VII in THF with (+)-pinanediol (1.7 g, 10.0 mmol) at room temperature under an argon atmosphere. After 1 hour, the reaction mixture is concentrated in vacuo and the resulting oil is purified by flash chromatography (4×14 cm column). The column is eluted with 80:20 n-hexane/ether to yield the desired compound VIII which is further purified by distillation under reduced pressure to give ptnanediol 3-bromopropane-1-boronate VIII as a colourless oil. B.p. 130° C./0.3 mm Hg, $[\alpha]_D^{20} = +22.9°$ (c=1,5 in $CHCl_3$)

C) (+)-Pinanediol-(S)-1-chloro-4-bromo-butane-1-boronate (IX)

A magnetically stirred, cooled (−104° C.) solution of 5 ml $CH_2Cl_2$ in 80 ml of THF (argon atmosphere) is treated for the formation of (dichloromethyl)lithium with n-BuLi (30 ml of a 1.6M solution in hexane, 48 mmol). After 30 min at −100° C., a solution of the chiral boronate (14.4 g, 47.8 mmol) in THF is added over a time period of 30 min. After stirring for additional 15 min. at −100° C., solid $ZnCl_2$ (3.3 g, 24.2 mmol freshly dried) is added to the reaction mixture.

After 15 min. at −100° C., the reaction mixture is warmed to room temperature and stirred for 2 hr. The resulting solution is concentrated in vacuo and an extractive workup (Ether/$H_2O$) is followed. The crude product is purified by flash chromatography (8×14 cm column, 97:3 n-hexane/gtOAc) to isolate the desired chiral α-chloro-boronate IX as a colourless oil. $[\alpha]_D^{20} = +36.4°$ (c=1 in $CH_2Cl_2$)

D) Z-D-Phe-Pro-Baa-OPin (XI)

This procedure is a one-pot 3-step procedure which comprises the in situ formation of a chiral α-(bistrimethylsilyl) amido boronate, the hydrolysis of the two trimethylsilyl groups and the coupling of the so formed α-amino boronate with the active ester V prepared in step A. The entire sequence of reactions is carried out under an argon atmosphere. The chiral α-chloro boronate IX of step C (3.5 g, 10.0 mmol) is dissolved in 35 ml of THF and the solution is cooled to −78° C. To this stirred solution is added lithium hexamethyldisilazane (10.0 ml of a 1.0M solution in n-hexane, 10 mmol). After stirring for 15 min at −78° C., the solution is warmed up to 15° C. and immediately recooled to −78° C. Methanol (0,8 ml, 20 mmol) is added, and then a solution of the active ester V of step A (4.93 g, 10.0 mmol) in 35 ml of THF is added to the in situ formed α-amino boronate. The mixture is stirred for 30 min at −78° C., warmed up to 0° C., stirred for 4 hr at this temperature and warmed further up to room temperature. After 15 hr, the mixture is filtered, the filtrate is concentrated in vacuo and the residue is purified by flash chromatography (4×14 cm column, 50:50 toluene/EtOAc) to give the desired chiral peptide boronate XI as a white foam. $[\alpha]_D^{20} = -64,6°$ (c=1 in $CH_2Cl_2$).

E) Z-D-Phe-Pro-BOMe-OPin (XII)

A magnetically stirred solution of NaOMe (227 mg, 4.2 mmol) in MeOH is treated with an equivalent amount of guanidine hydrochloride. The mixture is filtered and the solution containing free guanidine base is added over a period of 1.5 hr to a stirred solution of compound XI (3.0 g, 4.2 mmol) in 15 ml of MeOH.

After 20 hr at room temperature the obtained suspension is concentrated in vacuo. The residue is suspended in EtOAc and filtered to remove the insoluble material. The filtrate is concentrated and purified by flash chromatography (4×14 cm column, 50:50 toluene/EtOAc) to isolate Z-D-Phe-Pro-NH-CH--(($CH_2)_3$-$OCH_3$)-B-OPin (XII) as a white foam. $[\alpha]_D^{20} = -66.6°$ (c=1 in $CH_2Cl_2$).

Figure 3:
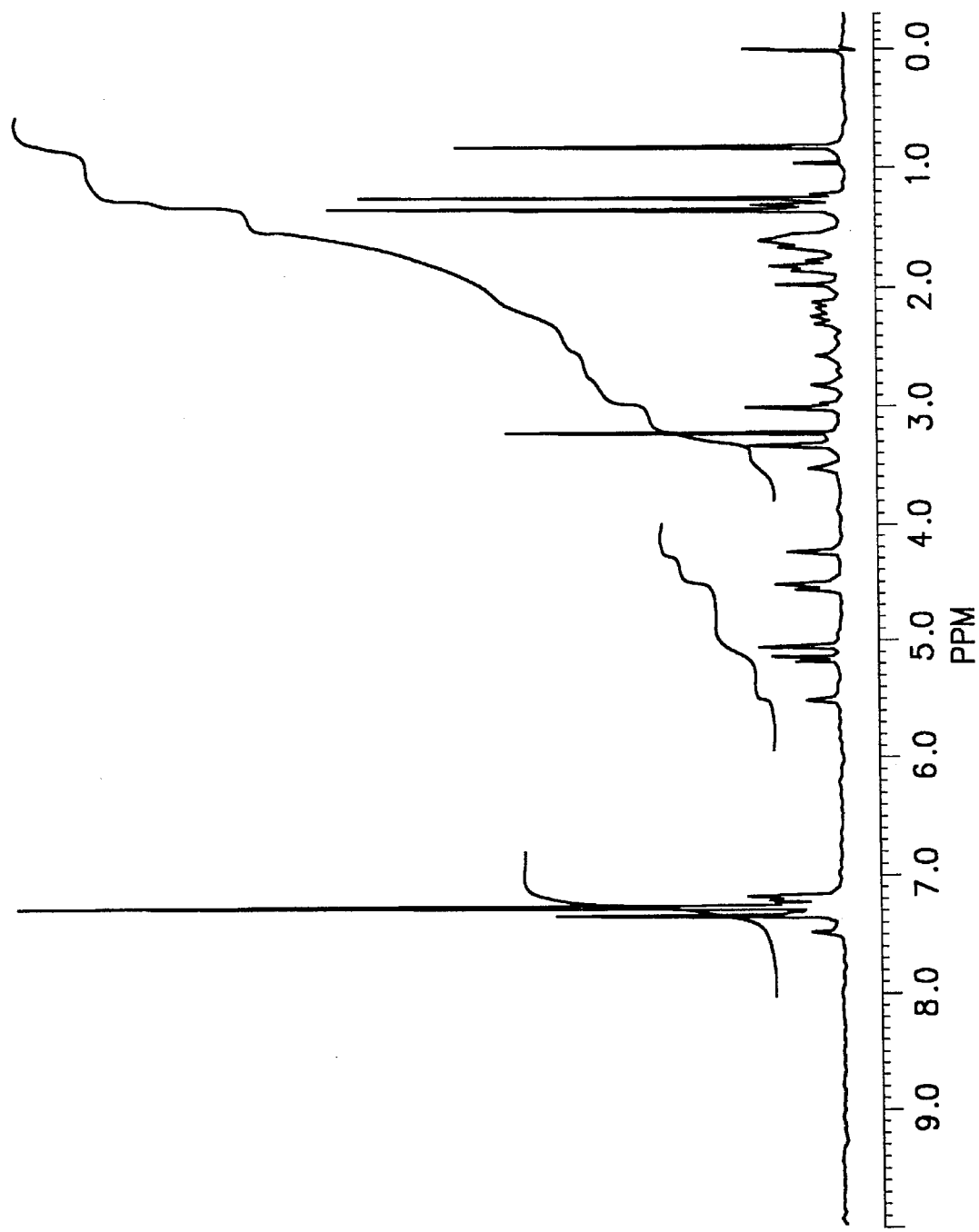
FIG. 3 depicts a proton NMR from 0 ppm to 9 ppm of the compound of formula XII, herein.
Figure 4:
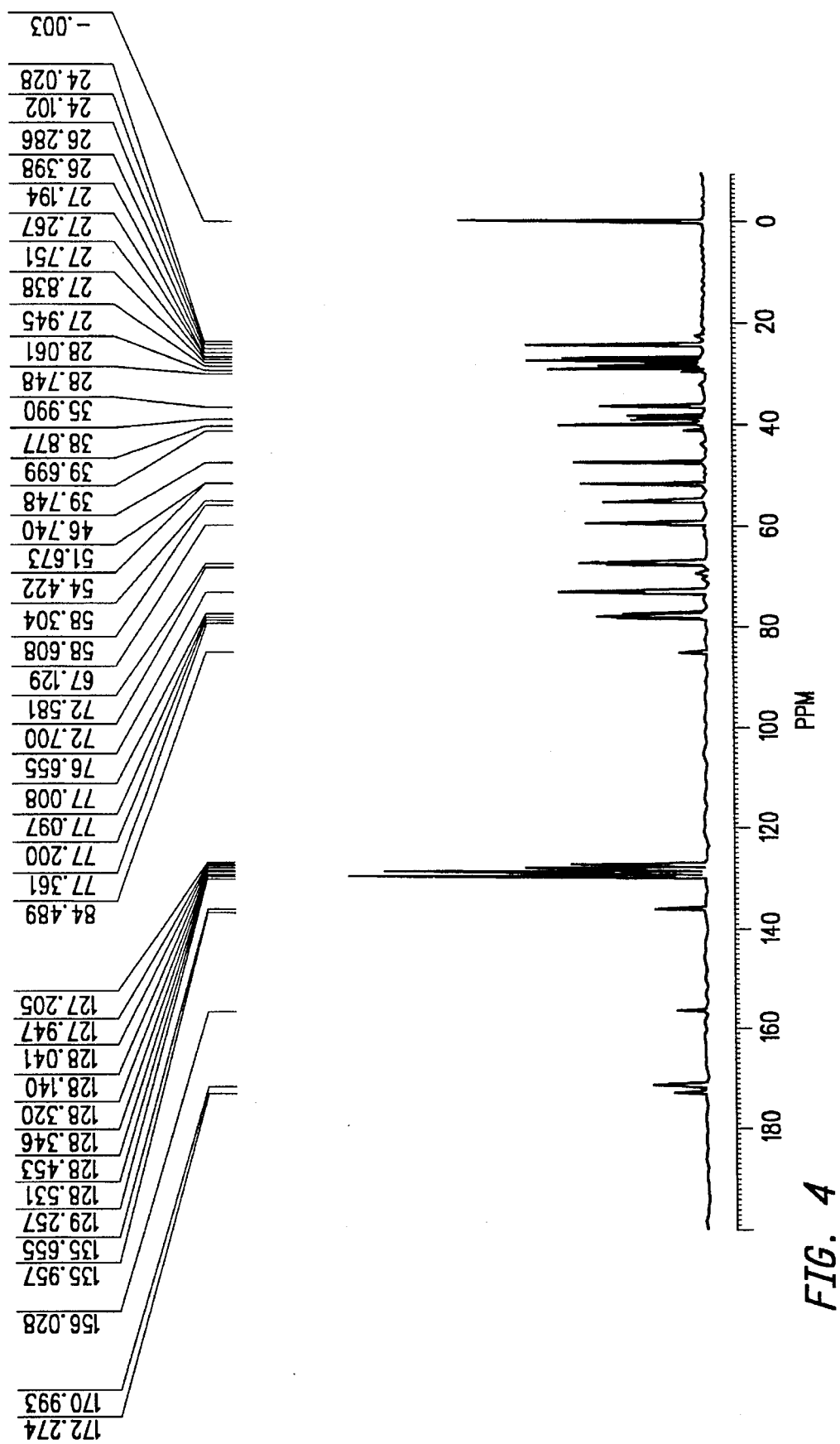
FIG. 4 depicts a $^{13}C$ NMR of the compound of formula XII, herein.

MS: $MH^+$ at m/e=660 proton NMR: see FIG. 3. singlet at 3.25 ppm (3 protons) due to methoxy group $^{13}C$ NMR: see FIG. 4. singlet at 58.305 ppm due to methoxy group.

The activity of the product as a thrombin inhibitor is measured by determination of the thrombin time essentially as described in European Patent Application 293 881, page 51. Using a 1 micromolar concentration of inhibitor, a mean thrombin time of 114 seconds is found, compared with 16 seconds in the absence of inhibitor.

EXAMPLE 3

A) Z-Phe-Baa-OPin

The procedure of Example 2 (D) is repeated using, in place of Z-D-Phe-Pro-ONSu, an equivalent amount of the product of Procedure F.

The product has a proton NMR ($CDCl_3$, 80 $MH_2$) with peaks at $\delta_H$ 0.78 (3, s); 1.23 (3, s); 1.30 (3, s); 3.0 (1, m); 3.28 (2, br-s); 4.28 (1, m); 5.0 (2, s); 5.18 (1, m); 5.93 (1, m); 7.23 (10–12, d).

(For each peak, the number in brackets indicates the number of protons, and s=single, br=broad, m=multiplet, d=doublet, t=triplet).

FAB Mass sprectrum (Fast Atom Bombardment spectrometer, 20 KV, $Cs^+$) 613 $[M+H^+]$ $Br^{81}$, 71%) 611 $[M+H^+]$ ($Br^{79}$, 30%).

B) Z-Phe-BOMe-OPin

To a solution of Z-Phe-Baa-OPin (0.28 g, 0.467 mmol) in MeOH (1 ml) is added over 1 hr a solution of NaOMe (30% solution in MeOH, 0.072 ml, 1 equivalent) and guanidine hydrochloride (45 mg, 1 equivalent), in MeOH (1 ml) with stirring under argon. After 16 hr TLC indicates little starting material and the solution is diluted by EtOAc (50 ml), washed with water (2×30 ml), and dried ($Na_2SO_4$). The organic phase is concentrated onto silica (grade 15111, 0.1 g) and applied to a silica column (grade 15111, 60 g, 3×24 cm). Elution by petroleum ether (b.p. 60°–80° C.): $CH_2Cl_2$:: 15:85 (v/v) (1.4L) and an increasing proportion of $CH_2Cl_2$ (200 ml), then elution by $CH_2Cl_2$ and an increasing proportion of MeOH (to 10%, 400 ml) gave starting material (60 mg, 0.098 mmol, 21%). Further elution (300 ml) gave the title compound 0.19 g, 0.34 mmol, 72.5%); $\delta_H$, 250 MHz, CDCl$_3$, 0.942 (3, s); 1.31 (3, s); 1.40 (3, s); 2.95 (1, m); 3.07 (1, m); 3.25 (3, s); 3.28 (2, m); 4.29 (1, unresolved d); 5.07 (2, s); 6.5 (1, v.br.s); 7.27 (10–12, m) FAB MS: [M+H$^+$] 563 (17%), 91 PhCH$_2$ (100%).

C) Ac-Leu-Leu-BOMe-OPin

Analogously to Example 3 B), but using an equivalent amount of Ac-Leu-Leu-Baa-OPin in place of Z-Phe-Baa-OPin, there is obtained the title compound as an oil, proton NMR: $\delta_H$ (CDCl$_3$, 250 MHz) 0.8–2.5 (aliphatic proton envelope); 2.0 (3, s); 2.9 (1, m); 3.25 (3, s); 3.26 (2, m); 4.24 (1, m); 4.5 (1, m).

FAB MS: 572 [M+Na$^+$] (22%), 551 [M+2H$^+$] (30%), 85 (100%).

D) Boc-Ile-Glu-(γ-piperidide)-Gly-BOMe-OPin

Analogously to Example 3 B) but using an equivalent amount of Boc-Ile-Glu(γ-piperidide)-Gly-Baa-OPin in place of Z-Phe-Baa-OPin there is obtained the title compound as a solid, proton NMR: $\delta_H$ (CDCl$_3$, 250 MHz) 0.95 (9, m); 1.0–2.6 (~40, aliphatic proton envelope); 3.4 (3, s); 3.9 (1, m); 4.0 (1, m); 4.2 (2, m); 5.05 (1, m).

We claim:

1. A method of inhibiting thrombin in the treatment of disease comprising administering to a mammal a therapeutically effective amount of a compound of the formula:

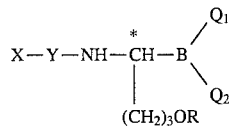

in which X=H or is an N-protecting group; Y is Phe-Pro; Q1 and Q2 taken together represent the residue of a diol; R is C$_{1-4}$ alkyl; and the asymmetric carbon atom marked * may have the D- or L- configuration.

2. The method of claim 1 wherein Q$_1$ and Q$_2$ together represent 2,3-dimethylbutandiol-2,3.

3. The method of claim 2 wherein X is benzyloxycarbonyl.

4. The method of claim 3 wherein R is CH$_3$.

5. The method of claim 1 wherein Q$_1$ and Q$_2$ together represent OPin.

6. The method of claim 5 wherein X is benzyloxycarbonyl.

7. A method of inhibiting thrombin in the treatment of disease comprising administering to a mammal a therapeutically effective amount of a compound of the formula: Z-D-Phe-Pro-BOMe-OPin.

8. A pharmaceutical composition comprising a pharmaceutically acceptable carrier and a pharmaceutically effective amount of a compound of the formula:

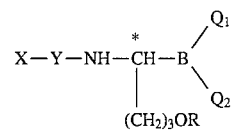

in which X=H or is an N-protecting group; Y is Phe-Pro; Q1 and Q2 taken together represent the residue of a diol; R is C$_{1-4}$ alkyl; and the asymmetric carbon atom marked * may have the D- or L- configuration.

9. The pharmaceutical composition of claim 8 wherein Q$_1$ and Q$_2$ together represent 2,3-dimethylbutandiol-2,3.

10. The pharmaceutical composition of claim 9 wherein X is benzyloxycarbonyl.

11. The pharmaceutical composition of claim 10 wherein R is CH$_3$.

12. The pharmaceutical composition of claim 8 wherein Q$_1$ and Q$_2$ together represent OPin.

13. The pharmaceutical composition of claim 12 wherein X is benzyloxycarbonyl.

14. A pharmaceutical composition comprising a pharmaceutically acceptable carrier and a pharmaceutically effective amount of a compound of the formula: Z-D-Phe-Pro-BOMe-OPin.

* * * * *

UNITED STATES PATENT AND TRADEMARK OFFICE
CERTIFICATE OF CORRECTION

PATENT NO.    : 5,574,014
DATED         : November 12, 1996
INVENTOR(S)   : CLAESON et al.

It is certified that error appears in the above-identified patent and that said Letters Patent is hereby corrected as shown below:

On title page, item [75]

Rainer Metternich should be deleted.

Signed and Sealed this

Seventh Day of September, 1999

Attest:

Q. TODD DICKINSON

*Attesting Officer*      *Acting Commissioner of Patents and Trademarks*